United States Patent [19]
White et al.

[11] Patent Number: 5,827,903
[45] Date of Patent: Oct. 27, 1998

[54] SEPARATION OF CATALYST FROM FISCHER-TROPSCH SLURRY

[75] Inventors: Curt M. White, Pittsburgh, Pa.; Michael S. Quiring, Katy, Tex.; Karen L. Jensen, Pittsburgh, Pa.; Richard F. Hickey, Bethel Park, Pa.; Larry D. Gillham, Bartlesville, Okla.

[73] Assignee: The United States of America as represented by the Department of Energy, Washington, D.C.

[21] Appl. No.: 594,969

[22] Filed: Jan. 31, 1996

[51] Int. Cl.$^6$ ............................ F16K 00/00; C07C 27/00; B01J 20/34; R01J 23/40
[52] U.S. Cl. .............................. 518/710; 502/22; 502/29; 502/326; 252/373
[58] Field of Search ............................... 502/22, 29, 326; 252/373; 518/710

[56] References Cited

U.S. PATENT DOCUMENTS 4,252,736   2/1981   Haag et al. .
4,423,265  12/1983   Chu et al. .
4,605,678   8/1986   Brennan et al. .

OTHER PUBLICATIONS

Separation of Fischer–Tropsch Catalyst/Wax Mixtures Using Dense Gas and Liquid Extraction, Apr. 1995.
Supercritical Fluid Technology, pp. 123–147 and pp. 265–280, edited by Penninger et al. (1985).
Chemical Engineering at Supercritical Conditions, pp. 419–433 (1983).
Status Review of Fischer–Tropsch Slurry Reactor Catalyst/Was Separation Techniques, Feb. 1991, prepared by P.Z. Zhou.
Fluid Phase Equilibria in Binary Ethylene + n–Alkane Systems, pp. 855–859, by Th. W. de Loos et al.
Solubilities of Solid N–Alkanes in Supercritical Ethane, by Moradinia et al., American Chemical Society, vol. 30, No. 3, pp. 40–45, (1985).

The Separation of Nonvolatile Substances by Means of Compressed Gases in Countercurrent Processes by Siegfried et al. pp. 746–750 (1978).
Analysis of Commercial Waxes Using Capillary Supercritical Fluid Chromatography –Mass Spectrometry by Hawthorne et al., J. of Chromatography, 388 (1987), pp. 397–409.
Cromatography With Sub–and Supercritical Eluents; Influence of Temperature, Prese and Flow–Rate on the Behavior of Lower Alkanes by Leyendecker et al, J. of Chromatoraphy, 321 (1985), pp. 273–286.
Abstract, "Separation of Fischer–Tropsch Catalyst/Wax Mixtures Using Dense Gas Extraction", April 2, 1995, Eyring et al.
Extended Abstract, "Separation of Fischer–Tropsch Catalyst/Wax Mixtures Using Dense Gas and Liquid Extraction", Sep. 10, 1995, White et al.

*Primary Examiner*—Gary Geist
*Assistant Examiner*—Karl J. Puttlitz, Jr.
*Attorney, Agent, or Firm*—Lisa M. Golke; Mark P. Dvorscak; William R. Moser

[57] ABSTRACT

In a catalytic process for converting synthesis gas including hydrogen and carbon monoxide to hydrocarbons and oxygenates by a slurry Fischer-Tropsch synthesis, the wax product along with dispersed catalyst is removed from the slurry and purified by removing substantially all of the catalyst prior to upgrading the wax and returning a portion to the Fischer-Tropsch reaction. Separation of the catalyst particles from the wax product is accomplished by dense gas and/or liquid extraction in which the organic compounds in the wax are dissolved and carried away from the insoluble inorganic catalyst particles that are primarily inorganic in nature. The purified catalyst free wax product can be subsequently upgraded by various methods such as hydrogenation, isomerization, hydrocracking, conversion to gasoline and other products over ZSM-5 aluminosilicate zeolite, etc. The catalyst particles are returned to the Fischer-Tropsch Reactor by slurring them with a wax fraction of appropriate molecular weight, boiling point and viscosity to avoid reactor gelation.

20 Claims, 2 Drawing Sheets

SEPARATION OF CATALYST FROM FISCHER-TROPSCH SLURRY

CONTRACTUAL ORIGIN OF THE INVENTION

The United States Government has rights in this invention pursuant to the employer-employee relationship of the Government to inventors as U.S. Department of Energy employees at the Pittsburgh Energy Technology Center and pursuant to Subcontract No. 8273-1898 with Kerr-McGee Corporation under US DOE Contract No. DE-AC22-89PC88400.

FIELD OF THE INVENTION

This invention relates to a catalytic process for converting synthesis gas, i.e., mixtures of gaseous carbon oxides with hydrogen or hydrogen donors, to hydrocarbon mixtures and oxygenates in the presence of a liquid suspension of catalyst and, in particular, relates to the dense gas and/or liquid separation of catalyst particles from the wax product which is produced.

BACKGROUND OF THE INVENTION

Processes for the conversion of coal and other hydrocarbon sources such as natural gas to synthesis gas are well known. Likewise, methane from natural gas or recovered from a coal bed or municipal landfill can be converted to synthesis gas mixtures of hydrogen with carbon monoxide or carbon dioxide. A summary of the art of gas manufacture, including synthesis gas, from solid and liquid fuels is given in the text and the references cited in the Background of the Invention of U.S. Pat. No. 4,605,678.

U.S. Pat No 4,605,678 teaches that it is desirable to effectively and more efficiently convert synthesis gas, and thereby coal and natural gas, to highly valued hydrocarbons such as motor gasoline with high octane number, petrochemical feedstocks, liquefiable petroleum fuel gas, high quality diesel, and aromatic hydrocarbons. It is well known that synthesis gas will undergo conversion to form reduction products of carbon monoxide, such as hydrocarbons, at temperatures in the range of from about 177° C. (350° F.) to about 454° C. (850° F.) and under pressure in the range of from about 1 to 1000 atmospheres, over a fairly wide variety of catalysts. The Fischer-Tropsch process, for example, which has been most extensively studied, produces a wide range of products including waxy materials, oxygenates and liquid hydrocarbons, a portion of which have been successfully used as low octane gasoline. The types of catalysts that have been studied for this and related processes include those based on metals or oxides of iron, cobalt, nickel, ruthenium, thorium, rhodium and osmium with and without promoters. As is well known in the art, such catalysts with various modifications encompass a wide range of conversion conditions for the reduction of carbon monoxide by hydrogen and provide flexibility toward obtaining selected boiling range products.

Often, the catalysts employed for Fischer-Tropsch synthesis are completely free from activators and consist essentially of the metals of Group VIII of the Periodic Table or their compounds only. It is thus desirable, and often required, to add suitable activating substances conventionally known and used for Fischer-Tropsch type synthesis. Copper, for example, is such an activating additive for iron catalyst. Cobalt or nickel may be activated by the addition of Th, Mg or Cu or their compounds. For a further increase in activity, alkali compounds are often added to the catalysts. Suitable alkali compounds are the oxides, hydro-oxides, carbonates, hydrocarbonates, phosphates, silicates and borates or sodium and potassium, furthermore their formates, acetates or the salts of higher organic acids, such as soaps.

The hydrogenation of carbon oxides to valued hydrocarbons by the Fischer-Tropsch process is highly exothermic and thus, the reaction system must include means to remove the heat of reaction. This is particularly important if a low $H_2/CO$ ratio synthesis gas is being converted, and also has significant importance during the conversion of high ratio synthesis gas. While low $H_2/CO$ ratio gas can be produced more cheaply than high $H_2/CO$ ratio gas, low $H_2/CO$ ratio gas cannot easily be converted to transportation fuels in conventional, fixed-bed Fischer-Tropsch reactors because of the difficulty in temperature control. The high temperatures of reaction and high carbon monoxide partial pressures favor carbon monoxide disproportionation and carbon formation which results in catalyst cementation.

For the purpose of furnishing better temperature control for Fischer-Tropsch type synthesis, in particular, if a low $H_2/CO$ ratio synthesis gas is converted, it has been proposed to suspend the finely divided catalyst in a liquid medium, preferably a hydrocarbon mixture such as may be, obtained by way of the higher boiling components of the synthesis products themselves. The suspension can then be subjected to cooling to continuously remove excess heat. The slurried-catalyst reactor system, otherwise identified as a suspended Fischer-Tropsch catalyst in a liquid medium suitable for the purpose of converting synthesis gas to hydrocarbon products is well known as is indicated in the early patents on the subject cited in U.S. Pat. No. 4,605,678.

In U.S. Pat. No. 4,252,736, the conversion of coal to gaseous and liquid products is achieved by the high efficiency gasification of coal to a low $H_2/CO$ ratio synthesis gas, conversion of the low ratio synthesis gas with a water gas shift slurry Fischer-Tropsch catalyst to a product comprising $C_1$ to $C_{900}$ hydrocarbons and oxygenates, and conversion of the Fischer-Tropsch product to premium gas and increased liquid products comprising gasoline, distillate and lubes over a special zeolite catalyst exemplified by ZSM-5. According to the patent, a coal, coke or coal char gasifier with a low steam to oxygen ratio as well as low steam to coal ratio has significant advantages in terms of thermal efficiency and cost and can lead to a reduction of up to 20 to 40 percent in synthesis gas production costs.

Any gasifier capable of producing a synthesis gas is applicable in the present invention. An important significance of U.S. Pat. Nos. 4,605,678 and 4,252,736 to the present invention is the efficiency which is gained by producing low $H_2/CO$ ratio synthesis gas. Such low ratio synthesis gas when reacted in a Fischer-Tropsch system is highly exothermic and as such a slurry Fischer-Tropsch process is desirable to remove process heat as previously described.

As is pointed out in U.S. Pat. No. 4,605,678, the organic product formed in a slurry Fischer-Tropsch process contains olefins, paraffins and oxygenated hydrocarbons with carbon numbers from 1 to about 80. In regard to the present invention, it is contemplated that carbon numbers from 1 to about 900 can be formed. Only those compounds vaporized at the reactor conditions plus some entrained molecules will appear in the overhead effluent. The remainder, a high molecular weight wax, remains in the slurry oil.

During normal operation, the high molecular weight wax is periodically withdrawn to prevent build-up of such wax in the reactor and to prevent gelation of the slurry and reactor shutdown. When such draw-off of the wax is made, the wax contains entrained catalyst particles which need to be removed prior to upgrading the wax and which must be available for use in the process. As discussed in U.S. Pat. No. 4,605,678, various magnetic, sintered-metal, and woven-wire cloth filters have been tested and found unsuitable for the conditions of temperature, pressure or particle size used in a Fischer-Tropsch reactor and none of the filtering methods investigated gave adequate throughput. A portion of the catalyst particles fines, however, are smaller than 1 micron in size such that ordinary filtration is ineffective for removal of fine catalyst particles and filtration using filter aids is time prohibitive and will not permit catalyst recovery. The process of U.S. Pat. No. 4,605,678, requires the equipment and expense to produce a high gradient magnetic field and is not applicable to nonmagnetic catalyst particles.

The separation of Fischer-Tropsch catalyst/wax mixtures has been recently reviewed in a document entitled "Status Review Of Fischer-Tropsch Slurry Reactor Catalyst/Wax Separation Techniques", prepared for U.S.D.O.E. Pittsburgh Energy Technology Center by P. Z. Zhou in February 1991 of the Burns and Roe Services Corporation under Contract No. DE-AC22-89PC88400 Subtask 43.02. A recent slurry phase Fischer-Tropsch experiment conducted at the LaPorte, Tex. Alternative Fuels Development Facility during the summer of 1992 failed to separate the Fischer-Tropsch catalyst/wax mixture by filtration. The filters clogged on the first day of operation.

Although separations of mixtures by dense gas and/or liquid extraction are well known, these techniques have not been applied to the separation of catalyst fines from hydrocarbon wax products. An excellent summary of the art is given in "Supercritical Fluid Technology" pages 123–147 and 265–280, edited by J. M. L. Penninger, M. Radosz, M. A. McHugh, and V. J. Krukonis, Elsevier, Amsterdam, 1985 and in, "Chemical Engineering At Supercritical Fluid Conditions" pages 419–433, edited by M. E. Paulaitis, J. M. L. Penninger, R. D. Gray, Jr. and P. Davidson, Ann Arbor Science Publishers, Ann Arbor, Mich., 1983.

The organic product formed in a slurry Fischer-Tropsch process contains olefins, paraffins and oxygenated hydrocarbons with carbon numbers from 1 to about 900. Only those compounds vaporized at the reactor conditions plus some entrained molecules appear in the overhead effluent. The remainder, a high molecular weight wax, remains in the slurry oil. At conditions which yield only a few percent methane, 25 percent by weight or more of the product may be high molecular weight wax. At certain reaction conditions the viscosity of the wax increases during reaction such that the slurry nears the point of gelation. A slurry medium is said to have gelled when it will not flow under gravity. If the slurry approaches gelation at reaction conditions, the reaction must be shut down.

Therefore in view of the disadvantages encountered in the prior art methods it is an object of the present invention to provide an improved process for catalytically converting carbon oxides and hydrogen in the presence of a finely divided catalyst in liquid suspension.

Another object of the invention is to provide an improved process for the removal of catalyst particles from the wax product which is recovered from a slurry Fischer-Tropsch reactor.

A further object is to provide an improved process for the recovery and recycle of catalyst particles which are contained in the high molecular weight products removed from a slurry Fischer-Tropsch reactor.

An object of the present invention is to provide an improved process for catalytically converting carbon oxides to hydrocarbons in the presence of a finely divided catalyst in liquid suspension.

Still another object is to remove undesirable compounds from the wax product of a slurry Fischer-Tropsch reactor in preparation for further upgrading of the purified wax.

Other objects will become apparent from the following description of the invention.

SUMMARY OF THE INVENTION

In accordance with the present invention, synthesis gas is converted to hydrocarbons in a Fischer-Tropsch reactor by contact with a catalyst dispersed in a liquid slurry. The catalyst has activity for reducing carbon monoxide to form hydrocarbons over a wide range of carbon numbers including hydrocarbon wax produced in the reaction zone. In order to control the viscosity and prevent gelation of the reaction slurry, wax product is removed along with a portion of the dispersed catalyst from the reaction zone. The wax product is mixed with a dense extractant fluid and a portion of the wax is extracted into the dense fluid. The dense fluid with its dissolved wax is separated from the insoluble catalyst and the catalyst is returned to the Fischer-Tropsch reactor. The dense extractant fluid is processed to reduce its density and thereby precipitate a wax product which is then separated from the dense fluid.

For purposes of the this application the term dense fluid is intended to mean a liquid, a dense gas, or a mixture thereof. The term "dense gas" refers to a gas (or supercritical fluid) at a pressure above atmospheric and with a density of at least one-twentieth that of the corresponding liquid just below its boiling point at atmospheric pressure. Preferably, the dense fluid will have a density of at least one-tenth that of the corresponding liquid hear its atmospheric boiling point. In this application the term "supercritical fluid" refers to a gas or gas mixture, in some instances with solute, at or above critical temperature and pressure.

In further aspects of the invention, the dense fluid, following separation of the wax product, is a gas and the gas is recompressed to increase its density prior to again mixing it with new wax product;

In other more specific aspects, the catalyst is a Fischer-Tropsch catalyst that is insoluble in the dense fluid and the dense fluid includes an extractant such as propane, n-butane, butene, n-pentane, hexane, toluene and mixtures thereof. The extractant can be obtained from the hydrocarbons formed in the Fischer-Tropsch reaction of this invention.

In other more specific aspects of the invention, a dense fluid is mixed with the wax product at supercritical pressure and temperature conditions, and after separation from the insoluble dispersed catalyst the density of the extractant fluid is reduced by decreasing its pressure by at least 5 atmospheres to cause the wax product to precipitate. The extractant gas is separated from the catalyst and wax product by density based separation and then recompressed for mixing with wax product withdrawn from the Fischer-Tropsch reactor.

In other more specific aspects of the invention, a liquid extractant is mixed with the wax product at subcritcal pressure and/or temperature conditions, and after separation from the insoluble dispersed catalyst the density of the extractant liquid is reduced by decreasing its pressure by at least 5 atmospheres which causes the wax product to precipitate. The extractant becomes a gas upon depressurization, and flows away from the precipitated wax and is then recompressed to the liquid state for mixing with wax product freshly withdrawn from the Fischer-Tropsch reactor.

In yet other aspects of the invention, a catalyst/wax mixture and dense fluid, are introduced tangentially into a settling vessel to facilitate the separation of the dispersed catalyst from the extractant. The extracted wax can be fractionated into molecular weight fractions as it is separated from the extractant by sequentially passing the fluid and the dissolved wax through a plurality of separating vessels in series with reductions in fluid density in each successive vessel to fractionate the wax product according to molecular weight. A light fraction of the wax or other upgraded fraction can be combined as needed with the recovered catalyst prior to return to the Fischer-Tropsch reactor.

In yet another aspect of the invention, the catalyst/wax mixture and the dense gas and/or liquid extracting solvent are introduced at or near the bottom of the first stage separator. The insoluble catalyst and any insoluble wax components remain in the first stage separator while soluble wax components are moved in the flowing solvent into the second stage where the solvent density is decreased and they are precipitated. This method of introduction into the first stage separator has the added benefit of allowing the flow of catalyst/wax to be temporarily stopped while continuing to introduce fresh solvent into the first separator that flows over the catalyst and wax components deposited in the first separator. This allows even those wax components that are very marginally soluble in the flowing solvent to be continuously extracted from the first separator and moved to the second separator.

The invention also contemplates a process for converting synthesis gas to hydrocarbons, the synthesis gas containing a low molar ratio of hydrogen to carbon monoxide obtained from the gasification of coal or other hydrocarbon feedstock. In the economic operation of coal gasifiers, low hydrogen/carbon monoxide ratios of not more than 1 to 1 and even as low as 0.4 to 1 are contemplated within the scope of this process. The process includes the steps of reacting $H_2$ and CO in a Fischer-Tropsch slurry reactor to produce hydrocarbons in the range of $C_1$ to $C_{900}$ including wax in the range of $C_{20}$ to $C_{900}$. The wax along with a portion of the catalyst is removed from the reactor, then mixed with an organic extractant fluid into which a portion of the wax is dissolved, and subsequently separated with the extractant from the catalyst which is returned to the Fischer-Tropsch slurry reactor. The wax is recovered from the organic extracting solvent by incremental reductions in the density of the solvent to decrease the solubility of the wax and precipitate the wax as a separate phase.

The present invention provides a process for converting synthesis gas comprising hydrogen and carbon monoxide to hydrocarbons by means of a slurry Fischer-Tropsch synthesis wherein a catalyst having activity for reducing carbon monoxide is dispersed in a liquid to form a slurry and a wax product is produced by the synthesis, characterized by removing the catalyst/wax mixture from the slurry and separating the removed mixture using a dense gas and/or liquid extractor where the wax components are soluble in the solvent and the catalyst particles are insoluble, characterized by separating the catalyst from the extract and recovering a purified wax product. The recovered catalyst is returned to the slurry Fischer-Tropsch reactor.

In accordance with the present invention, the wax product recovered from a slurry Fischer-Tropsch reactor is purified to the extent that substantially all of the catalyst particles are separated from the wax product prior to wax upgrading. The catalyst particles are recycled into the slurry Fischer-Tropsch reactor. Separation of the catalyst particles from the wax product is accomplished by dense gas and/or liquid extraction in which the organic compounds in the wax are dissolved and carried away from the insoluble inorganic catalyst particles that are primarily inorganic in nature. The purified catalyst free wax can be subsequently upgraded by various methods such as hydrogenation, isomerization, hydrocracking, conversion to gasoline, distillate, and/or lubes over ZSM-5 aluminosilicate zeolite, etc.

DESCRIPTION OF THE DRAWING

The present invention is illustrated in the accompanying drawings wherein.

DETAILED DESCRIPTION OF THE INVENTION

Figure 1:
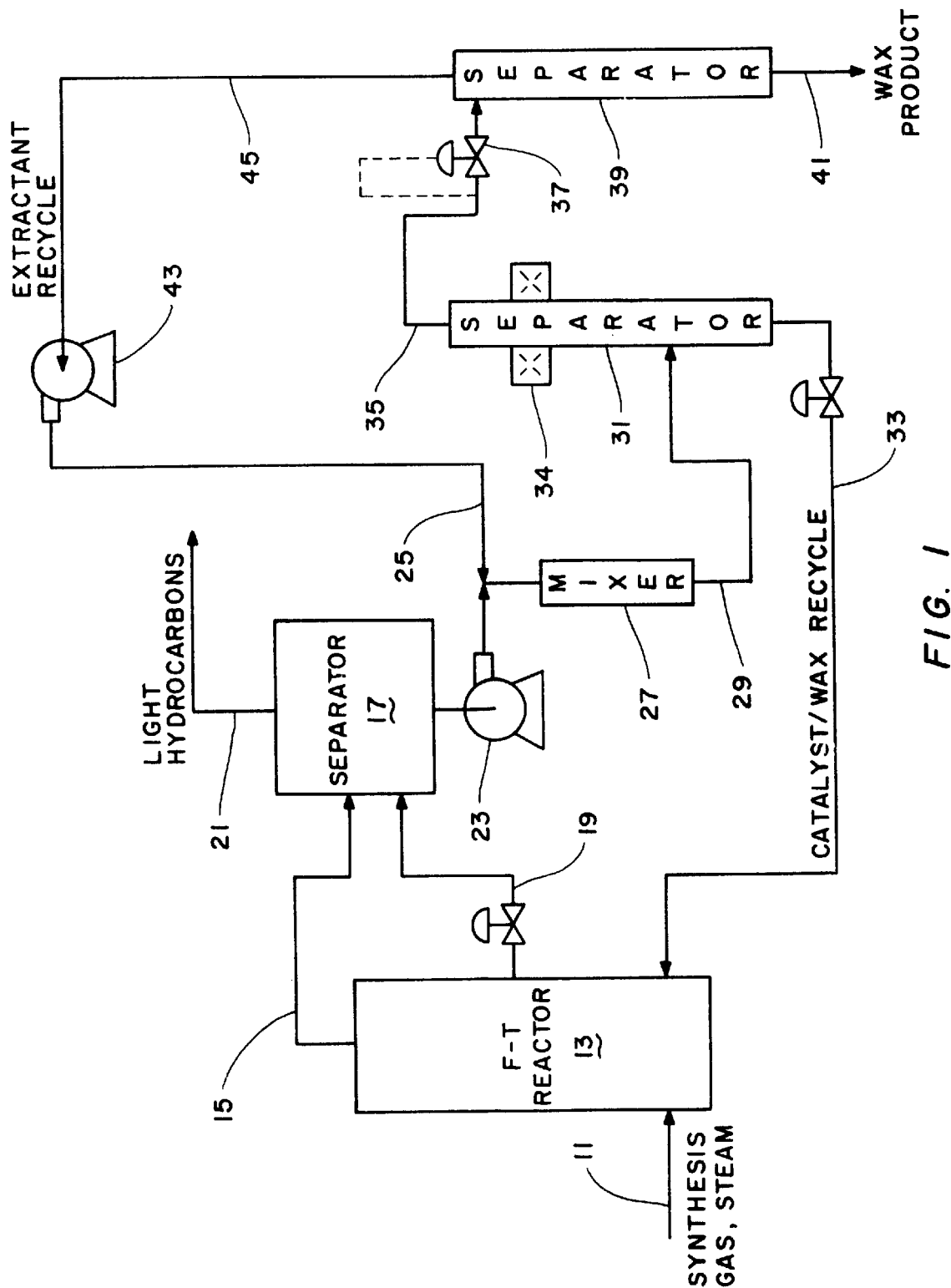
FIG. 1 is a schematic diagram of a slurry Fischer-Tropsch process for converting synthesis gases and separating catalyst particles from the wax product.

The preparation of synthesis gas by coal gasification and the Fischer-Tropsch conversion of the carbon monoxide and hydrogen thus formed to hydrocarbons in a catalytic slurry reactor are described in U.S. Pat. No. 4,605,678. This U.S. patent is hereby incorporated by reference and portions incorporated herein for this purpose.

The synthesis gas used is typically a conventional gas mixture as used in the synthesis of hydrocarbon products in a Fischer-Tropsch, carbon monoxide hydrogenation procedure. The synthesis gas can include the product of coal gasification, methane (natural gas) conversion or gas generated in any other suitable manner well known in the art for this type of reaction. The charge for the slurry Fischer-Tropsch reactor may contain an excess or shortage of hydrogen in respect to the stoichiometric equivalent, such as about 4 moles of hydrogen per mole of carbon oxide, preferably carbon monoxide. However, the ratio of reactants may be varied within fairly wide limits as recognized in the art.

For instance, a coal or char gasifier producing low ratio $H_2/CO$ synthesis gas requires less investment than that to produce high $H_2/CO$ ratio synthesis gas because of the large steam and oxygen requirements for high ratio gas. Because of these large and significant differences in investment and energy requirements in preparing steam and oxygen, the relative amounts of these reactants required in a char or coal gasification operation have an important bearing on the thermal efficiency of the process. That is, the highest efficiency occurs at the lowest steam to oxygen ratio that satisfies the stoichiometry for an $H_2/CO$ ratio gas of about 0.50 and the operating temperature constraints of the operation.

Low ratio synthesis gas ($H_2/CO=1/1$ or less) is not detrimentally critical to this process, and utilization of a Fischer-Tropsch catalyst containing or provided with water gas shift characteristics in the slurried catalyst reactor system can be relied upon for effecting high conversions of $H_2$ and CO when processing both low and higher ratio synthesis gas feed. It is much less costly to generate a low $H_2/CO$ synthesis gas, 1/1 or less, than it is to generate a higher ratio synthesis gas. Furthermore, a low ratio synthesis gas in the range of 0.4 to 0.7 can be adjusted by the water gas shift activity of a Fischer-Tropsch catalyst on a once-through basis to provide high yields of $C_3$+hydrocarbons and oxygenates.

If a low ratio synthesis gas (1/1 or less $H_2$/CO ratio) is charged, it is essential that the carbon monoxide reducing catalyst used include water gas shift activity or characteristics so that steam formed in the Fischer-Tropsch operation by conversion of the low ratio synthesis gas will react with charged CO to form $H_2$. Examples of carbon monoxide reducing catalysts comprising shift activity are iron alone, or iron, cobalt, or ruthenium provided with an added shift catalyst component. Shift catalysts suitable for the purpose include those containing the elements Fe, Cr, Zn or Cu. It is also contemplated charging some steam with the synthesis gas of 0.7 $H_2$/CO ratio or less.

It is important for temperature control in the slurried Fischer-Tropsch operation to maintain sufficient heat exchange liquid generally comprising a relatively high boiling portion of the synthesis hydrocarbon product in direct contact with the catalyst particles to substantially suspend the particles and maintain predetermined and desired temperature control and thus limit the buildup of coke on the catalyst particles. Thus, it is possible in the liquid phase slurry Fischer-Tropsch operation to more closely restrict the temperature rise due to exothermic reaction about any given particle within more narrow limits, to use more selective operating temperatures, and achieve results not obtainable in a fixed bed catalyst system. The level of liquid in the slurry reaction zone is maintained at desired level by the continuous withdrawal of vapors and liquid product that contains catalyst. The recycle of a liquid product with catalyst particles to the reaction zone following temperature adjustment is pursued as required.

The liquid used for the suspension of the catalyst is preferably a hydrocarbon oil product which will not appreciably volatilize under the temperature and pressure at which carbon monoxide hydrogenation proceeds in the Fischer-Tropsch reaction. Thus, for instance, it is preferred to use a hydrocarbon oil product (wax) fraction having a boiling point generally somewhat higher than the highest reaction temperature that is to be used in the conversion. Accordingly, hydrocarbon product oil fractions boiling above 250° C. are normally satisfactory. However, it is advantageous to use for the suspension of the catalyst an oil product as is obtained in the Fischer-Tropsch synthesis itself and having the requisite boiling range.

The catalysts used in accordance with the invention are inorganic metals or metal compounds that are not generally soluble in organic solvents. Thus, as will be described below, organic wax products are separated from the catalysts by solvent extraction into a dense organic fluid in accordance with the invention. In general, the catalyst used may be any suitable catalyst conventionally employed for carbon monoxide hydrogenation with the Fischer-Tropsch type synthesis. Such catalysts contain, as known, metals of Group VIII of the Periodic Table, including iron, nickel, cobalt and ruthenium. To the extent that the catalyst employed for the synthesis in liquid medium in accordance with the invention is completely free from activators or consist of the Group VIII metals or their compounds only, it is desirable to add suitable activating substances conventionally known and used for synthesis of the Fischer-Tropsch type. Such activating substances include metals such as copper, thorium or magnesium or their compounds in quantities which do not exceed more than a few percent of the Group VIII metal catalyst. Additional increases in activity can be achieved by adding alkali compounds to the catalyst such as potassium or sodium. Suitable alkali compounds are the oxides, hydrooxides, carbonates, hydrocarbonates, phosphates, silicates and borates of sodium and potassium, furthermore their formates, acetates or the salts of higher organic acids, such as soaps. In addition to the above, catalysts of nonmagnetic material such as cobalt also may be selected and separated from wax product in accordance with the invention.

In general, the Fischer-Tropsch synthesis reaction will be carried out at well known operating conditions. Preferably, a low $H_2$/CO ratio synthesis gas, 0.1 to 1 and more usually in the range of 0.5 to about 0.8 which is typically obtained by high efficiency gasification of coal as set forth in detail in U.S. Pat. No. 4,252,736 incorporated herein by reference, is converted in the slurry catalyst Fischer-Tropsch reactor at a temperature within the range of about 200° C. (392° F.) up to about 320° C. (608° F.) and a pressure within the range of about 3 to 70 atmospheres (44 to 1030 psig). Synthesis gas derived from methane with $H_2$/CO ratio near 2 can also be used. The contact time of the synthesis gas is chosen to provide high conversion per pass, at least 50 percent, preferably 70 to 95 percent. This value depends on the length of the reactor, the nature of the Fischer-Tropsch catalyst and its concentration in the slurry. The preferred catalyst is one comprised of 100 parts Fe, 0.3 to 3.0 parts Cu and 0.1 to 1.5 parts $K_2CO_3$ by weight. Precipitated catalysts are preferred over supported catalysts. A space velocity between about 0.5 liter and 10 liters of synthesis gas (STP) per gram iron per hour will provide the desired high conversion. Catalyst concentrations of 20 to 50% can be used in slurry phase Fischer-Tropsch reactors. Within these operating parameters, the temperature exotherm encountered by any given suspended catalyst particle in the liquid phase material is closely retained within the narrow limits, thereby contributing to a more satisfactory operation of the system for producing liquid products. The suspended catalyst particles retained in the liquid phase may be selected from within the range of about 1 to 50 microns, thereby providing a larger amount of surface-active sites than obtainable with larger size catalyst particles or extrudate used in fluid and fixed catalyst bed systems. The low temperature operation contemplated is particularly desirable for reducing the production of $C_1$ and $C_2$ hydrocarbons, for reducing carbon buildup on the catalyst and for improving selectivity operation for producing liquid hydrocarbon. Thus, not only is the liquid product selectively maintained high by the low temperature liquid slurry Fischer-Tropsch operation, but the use of a low cost gasifier which reduces synthesis gas production costs from 20 to 40 percent can be used to advantage with the slurry Fischer-Tropsch catalyst operation.

Optionally, a product of the Fischer-Tropsch synthesis operation separated from catalyst particles, other than that required for recycle to maintain the desired liquid phase, can be recovered for further processing as in U.S. Pat. No. 4,252,736. This recovered material comprising liquid and gaseous components of the Fischer-Tropsch operation may be separated to recover oxygenates and $C_4$–gaseous components therefrom for treatment separately from $C_5$+gasoline and distillate boiling range hydrocarbons, or a total product mixture thereof without separation is passed in contact with a separate bed of the special zeolite catalyst and particularly represented by ZSM-5 zeolite. The special zeolite catalyst is maintained under particularly desired activity and selectivity conditions to convert ethylene, $C_3$+or $C_5$+hydrocarbons with and without oxygenates either separately or together to hydrocarbon products including higher octane gasoline boiling range products and/or distillate fuels and lubes.

The process of the present invention can be described in reference to the Figures. In FIG. 1, a synthesis gas feed 11 along with steam, when needed to supplement $H_2/CO$ ratio, is fed to a slurry Fischer-Tropsch reactor 13 operated as described above. Carbon oxides, particularly carbon monoxide in the synthesis gas, react in the presence of a Fischer-Tropsch catalyst with water gas shift activity to form hydrocarbons and oxygenates with carbon contents of about $C_1$ to $C_{900}$. Hydrocarbon and oxygenate waxes of $C_{20}$ to $C_{900}$ if allowed to accumulate in Reactor 13 as discussed above, will result in increased viscosity and gelation. Gas phase products with entrained liquid wax and catalyst particles are removed at 15 and passed to Separator 17, but if additional wax product must be removed, periodic withdrawals are made through line 19 of slurry containing wax and dispersed catalyst. Light hydrocarbons 21, separated from liquid and dispersed solids in separator 17, are removed for further processing and use as product, for instance by conversion in the presence of ZSM-5 as disclosed in U.S. Pat. No. 4,252,736. The wax product and dispersed catalyst are pumped at 23 to an elevated pressure and mixed i.e. with a dense extracting fluid such as a dense gas and/or liquid extractant 25 in mixer 27. Mixer 27 can be any type of mixing device suitable for blending high pressure liquid slurry with a high density gas, supercritical fluid, and/or liquid serving as an extracting solvent. For example a stationary mixer such as a static tube mixer is particularly well suited for use in the present invention as it provides ample contact and dispersion between the liquid slurry and the extracting solvent to begin the dissolution of the organic hydrocarbons and oxygenates into the solvent.

The mixture of extractant loaded with dissolved and undissolved wax products and catalyst leaving Mixer 27 at 29 passes to a density based separator 31 such as a setler in which the insoluble catalyst is removed for recycle at 33 to the Fischer-Tropsch reactor 13. In a settling type separator, a tangential entry is preferred to achieve an initial centrifugal separation of the catalyst from the dense fluid. Alternately, the mixture of extractants loaded with dissolved and undissolved wax products and catalyst leaving mixer 27 at 29 can be introduced at or near the bottom of separator 31. Separator 31 provides additional contact time for dissolution of the wax into the extracting solvent, but extraction conditions can be adjusted such that only a portion of the wax dissolves and a portion remains with the insoluble catalyst. Although not shown, appropriate fractions of catalyst-free product liquid can be added to the catalyst particles to make up for loss, and to maintain the desired boiling point and viscosity of the Fischer-Tropsch slurry. The dense fluid with extracted product wax at 35 is reduced in density, for instance by pressure reduction at regulating valve 37 and introduced into separator 39 where wax product, substantially free of dispersed catalyst, is precipitated and removed at 41 for further upgrading and processing. It is to be understood that the density of the loaded extracting gas and/or liquid also may be reduced by increasing temperature to reduce solubility and separate the product wax. As illustrated, compressing or pumping device 43 withdraws and recompresses the extracting fluid from separator 39 through line 45 for reuse in mixer 27.

Figure 2:
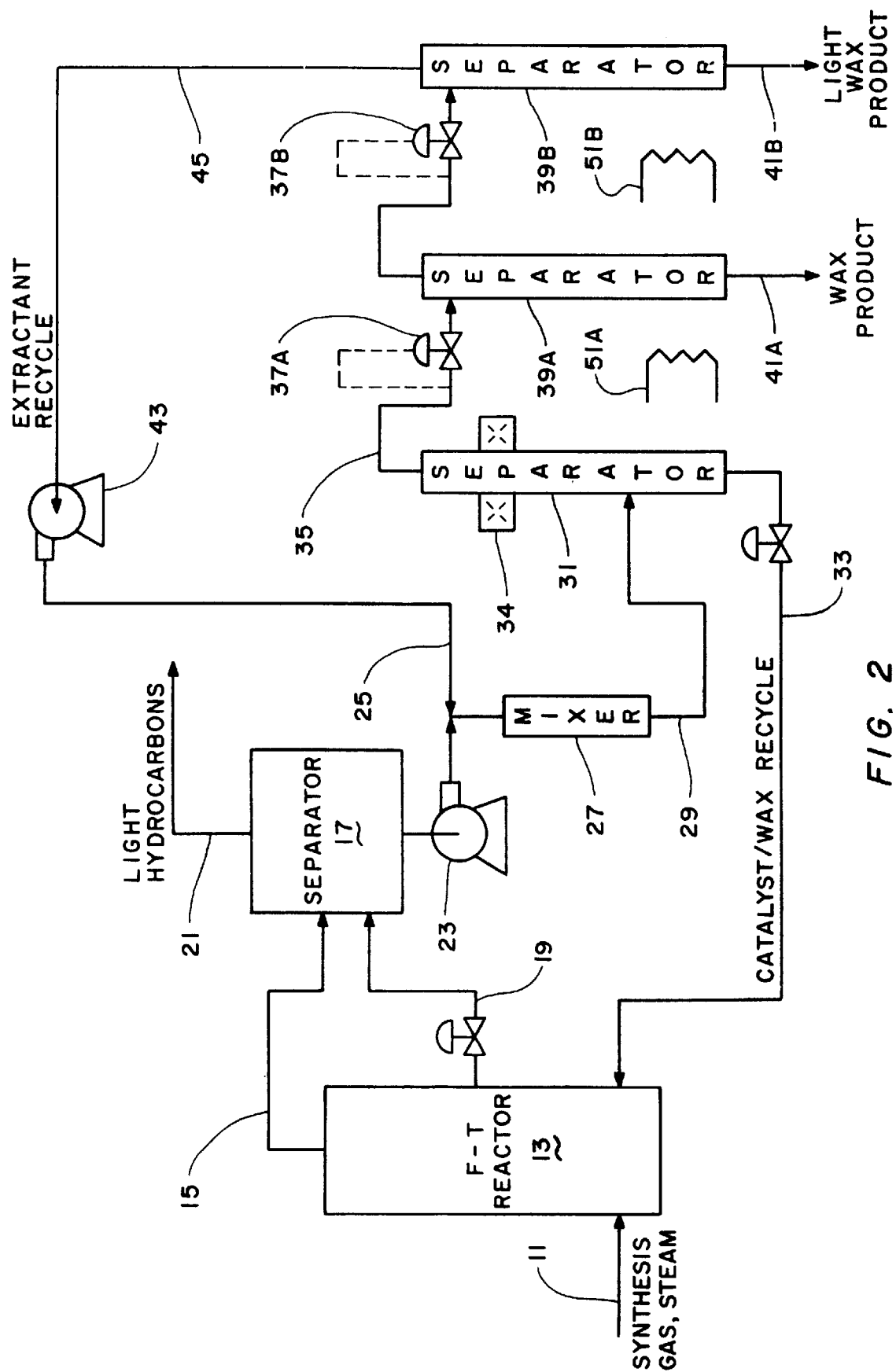
FIG. 2 is a schematic diagram of an alternative arrangement of a catalyst/wax separation process suitable for use with a Fischer-Tropsch process.

When extraction is used in conjunction with magnetic field separation, the electromagnets are added to the interior and/or exterior of separator 31 as illustrated at 34 in FIGS. 1 and 2. Where electromagnetic separation of fine particles is used with separator 31 an additional separating step, such as fine particle filtering can be used to remove catalyst from wax product 41. A demagnetizer (not shown) can be added to demagnetize the catalyst before it is returned to the Fischer-Tropsch Reactor.

The separation process also can be performed in a plurality of separation vessels as is illustrated in FIG. 2 with like reference numbers designating like elements of the drawing. A plurality of separator vessels 31, 39A, 39B are shown interconnected in series by means of valves 37A and 37B to effect a plurality of sequential pressure reduction steps for the stepwise reduction of density, and the fractionation of the catalyst free wax product as indicated at 41A and 41B. Optionally, electromagnetic means 34 can be used to limit any fine catalyst carryover into separators 39A and 39B, thereby providing a cleaner wax product 41A and 41B. Typically, the heavier and higher molecular weight wax will be recovered in fraction 41A and the lighter fraction at 41B.

Also illustrated in FIG. 2 are heater coils 51A and 51B as supplemental or alternative means for affecting density changes in the dense extractant gas and/or liquid. In addition, heater coils 51A or 51B can be used for vaporizing lighter components and thereby drive them into the extractant recycle at 45. If desired a portion of recycle 45 can be condensed and refluxed to separator 39B to effect a distillation separation.

Therefore, dense organic extractant gases and/or liquids can be used to dissolve the wax components from the catalyst/wax slurry, leaving the insoluble metal-containing catalyst and any insoluble wax components behind. The insoluble metallic catalyst can be recycled back to the slurry Fischer-Tropsch reactor. Extraction conditions can be adjusted such that only a portion of the wax dissolves in the extracting solvent and a portion of the wax remains with the catalyst. When a portion of the wax remains with the catalyst the mixture is still a slurry and can be pumped. Alternatively, the wax components can be extracted to produce a dry solid material containing the catalyst. Under these conditions, a portion of the catalyst free wax can be added back to the catalyst to form a pumpable slurry.

The extractant used can be one or more of those produced by the Fischer-Tropsch reaction, including such compounds as $CH_4$, $C_2H_6$, $C_3H_8$, $C_4H_{10}$, $C_5H_{12}$, $C_6H_{14}$, $C_2H_4$, $C_3H_6$, $C_4H_8$, $C_4H_6$, $CO_2$ and mixtures thereof in the liquid state, or as dense gases. Any compressed gas, gaseous mixture or liquid can be used that dissolves the wax and not the catalyst. Some of the above solvents have critical points that are not far, in terms of temperature and pressure, from the temperatures and pressures ordinarily used in the operation of a Fischer-Tropsch slurry reactor as described. Below, near and above the critical point, these compounds are expected to display considerable solvating power. Thus, it is possible to extract the wax product components from the solid metallic catalyst using dense gas and/or liquid extraction. The metallic catalyst is insoluble in the above mentioned solvents and thus remains behind. Once the dense extracting fluid stream containing the dissolved wax flows away from the insoluble catalyst and into another vessel, and its density reduced, the solvent looses its solvating power, and the catalyst free wax components precipitate out of solution.

Organic liquids such as pentane ($C_5H_{12}$), isopentane ($C_5H_{12}$), hexane ($C_6H_{14}$), toluene ($C_7H_8$), cyclohexane ($C_6H_{12}$), hexene ($C_6H_{12}$), methanol ($CH_4O$), acetone ($C_3H_6O_8$), or liquid mixtures can also be used as the extracting solvent.

Another way to force the wax components from solution is to heat the mixture of dense extracting solvent and wax components. The solvating power of these dense gas and liquids are directly related to their density. The denser the solvent, the greater its solvating power. Since heating a dense solvent causes its density to decrease, heating will also cause the solvating power of the solvent to decrease, thus forcing the wax components out of solution.

Removal of substantially all of the fine catalyst particles from the wax product has been achieved by dense gas and/or liquid extraction as disclosed herein as shown in Tables 1 and 2. The separation system of the present invention is remarkably efficient in removing small catalyst particles which are in the hydrocarbon products from the slurry Fischer-Tropsch reactor. It is believed that the selective solvation of wax components and not catalyst particles is the primary reason for the efficient separation observed.

EXAMPLE I

The following examples in Table 1 illustrate the ability of a solvent to remove wax product from catalyst from a Fischer-Tropsch slurry reactor. In carrying out the separations of Table I, a process similar to that illustrated in FIG. 1 was used with a dense fluid mixture of n-butane and catalyst/wax feed (to separator 31) at temperatures above and below the critical temperature (152° C.) of n-butane and at a pressure greater than the critical pressure of n-butane (37.5 atmospheres). The density of the fluid was reduced by increasing the temperature in separator 39 by at least 15 centigrade degrees.

TABLE 1

Examples
Separation of Catalyst Particles From
Fischer-Tropsch Slurry Reactor

| extraction solvent | weight % catalyst in feed | weight % catalyst in product from first stage separator | weight % catalyst in product from second stage separator |
| --- | --- | --- | --- |
| n-Butane | 4.91 | 8.6 | <0.01 |
| n-Butane | 4.91 | 11.1 | <0.01 |
| n-Butane | 4.91 | 13.4 | <0.01 |
| n-Butane | 4.91 | 24.8 | 0.03 |

EXAMPLE 2

The results listed below in Table 2 illustrates the ability of solvent to remove wax product from catalyst from a Fischer-Tropsch slurry reactor. In carrying out the separation in Table 2, a process similar to that illustrated in FIG. 1 was used with liquid n-butane, and a catalyst/wax feed (to separator 31) at a temperature of 138° C. and a pressure of about 70 atmospheres (1018 psig). The n-butane was reduced in pressure to about 7.8 atmospheres (100 psig) in separator 39 at a temperature of 138° C.

Table 2. N-butane (Tc=152° C., Pc=550 psi) and no magnets. Feed was 4.91 wt % catalyst in wax.

TABLE 2

| 1'st sep temp °C. | 2'nd sep temp °C. | 1'st sep press psig | 2'nd sep press psig | 1'st sep wt % feed | 2'nd sep wt % feed | wt % feed rec | wt % cat 1'st sep | wt % cat 2'nd sep |
| --- | --- | --- | --- | --- | --- | --- | --- | --- |
| 138 | 138 | 1018 | 100 | 2.0 | 82.1 | 96.9 | 22.6 | 0.11 |

Another example using n-butane is given in Table 3 and illustrates the ability of solvent to remove wax product from catalyst from a Fischer-Tropsch slurry reactor. In carrying out the separation in Table 3, a process similar to that illustrated in FIG. 1 was used with liquid n-butane, and a catalyst/wax feed (to separator 31) at a temperature of 107° C. and a pressure of about 51 atmospheres (750 psig). The first stage separator was equipped with an external magnet to minimize carry over of iron catalyst particles to the second stage separator. The n-butane was reduced in pressure to about 3 atmospheres (42 psig) in separator 39 at a temperature of 107° C.

Table 3 N-butane (Tc=152° C., Pc=550 psi) and magnets external to the first stage separator (31). Feed was 4.91 wt % catalyst in wax.

TABLE 3

| 1'st sep temp °C. | 2'nd sep temp °C. | 1'st sep press psig | 2'nd sep press psig | 1'st sep wt % feed | 2'nd sep wt % feed | wt % feed rec | wt % cat 1'st sep | wt % cat 2'nd sep |
| --- | --- | --- | --- | --- | --- | --- | --- | --- |
| 107 | 107 | 750 | 42 | 6.57 | 76.8 | 105 | 72.6 | 0.04 |

EXAMPLE 3

In a process using equipment similar to that of FIG. 2, a Fischer-Tropsch reactor operated at a temperature of 270° C. and 55 atmospheres pressure discharges its product into a vapor liquid separator where the heavy organic product containing 4.91 wt % entrained iron catalyst is mixed with dense supercritical pentane gas at 55.4 atmospheres (800 psig) and a temperature of 204° C. After separating the catalyst and any insoluble wax components in the first stage separator, the dense pentane and any soluble wax components are swept to the second stage separator where the pentane density is reduced by dropping the pressure to about 3 atmospheres, and where a portion of the wax product having carbon numbers in the range of about $C_{20}$ to $C_{350}$ is precipitated. On expansion into the third stage separator held at 1 atmosphere and more than 30° C. essentially all the remaining light wax components are deposited in separator 39B while the gaseous pentane is removed via 45 and recompressed at 43 for mixture with fresh catalyst/wax slurry. All of the wax product from the second and third separators is found to have less than 0.1 wt % catalyst. Actual results from two experiments using pentane as the extracting solvent and magnets external to the first stage separator to aid in minimizing carry over of the iron catalyst to the second separator are shown in Table 4.

Table 4. N-pentane (Tc=196.5° C., Pc=485.5 psi) and magnets external to the first stage separator (31). Feed was 4.91 wt % catalyst in wax.

TABLE 4

| 1'st sep temp °C. | 2'nd sep temp °C. | 3'rd sep temp °C. | 1'st sep press psig | 2'nd sep press psig | 3'rd sep press psig | 1'st sep wt % feed | 2'nd sep wt % feed | 3'rd sep % feed | wt % feed rec | wt % cat 1'st sep | wt % cat 2/nd sep |
|---|---|---|---|---|---|---|---|---|---|---|---|
| 204 | 204 | <30 | 800 | 43 | 0 | 5.9 | 73.1 | 9.8 | 98.1 | 63.6 | 0.05 |
| 204 | 204 | <30 | 800 | 33 | 0 | 4.2 | 69.6 | 15.3 | 95.9 | 50.6 | 0.01 |

EXAMPLE 4

In a process similar to that illustrated in FIG. 2, a Fischer-Tropsch reactor operated at a temperature of 270° C. and 55 atmospheres pressure discharges its product into a vapor liquid separator where the heavy organic product containing entrained iron catalyst is mixed with dense supercritical hexane gas at 55.4 atmospheres (800 psig) and a temperature of 240° C. (464° F.). After separating the catalyst in a small amount of wax for recycle to the Fisher Tropsch reactor, the dense hexane with dissolved wax is passed to a second separator with a pressure and temperature reduction to about 2 atmospheres and 197° C. where a portion of the wax product having carbon numbers in the range of about $C_{20}$–$C_{350}$ is removed. On expansion into the third separator at one atmosphere pressure and 70° C. essentially all of the hexane and lower hydrocarbons are separated from the light wax product, which remains in separator 39 while the gaseous hexane is removed via 45 and recompressed at 43 for mixture with fresh catalyst/wax slurry. All of the wax product from the second and third separators is found to have less than one tenth percent by weight catalyst. Actual results using hexane as the extracting solvent and magnets in the first stage to aid in minimizing carry over of iron catalyst to the second separator are shown in Table 5.

Table 5. N-hexane ($T_c$=234.2° C., Pc=437.0 psi) and magnets external to the first stage separator. Feed was 4.91 wt % catalyst in wax.

particles are separated from the wax by centrifugation, 3) high gradient magnetic field separation where Fischer-Tropsch catalysts containing iron or another magnetic particle are separated from nonmagnetic organic wax components as described in U.S. Pat. No. 4,605,678, and 4) filtration devices where a melted catalyst/wax mixture is separated by passing the wax components through a filter and collecting the catalyst particles on a filter. Recycle of the catalyst to the slurry reactor is performed irrespective of whether the dense gas and/or liquid extraction separation system is used alone or in combination with other separation systems.

The dense-gas/liquid extraction process described here for recovery of Fischer-Tropsch catalyst from wax is useful in other catalytic polymerization process for the separation of catalyst from oligomeric products. Recovery of catalysts from the production of polyethylene and other olefin polymerization process is an example. The technology is also useful in recovery of any heterogenous catalyst where the reaction mixture is soluble in the extracting solvent but the catalyst is insoluble in the extracting solvent. For example, the recovery of metallic hydrodesulfurization and hydrodenitrogenation catalysts used in the petroleum industry to process petroleum products.

Although the present invention has been described with reference to details of the illustrated embodiment, these details are not intended to limit the scope of the invention as defined in the appended claims.

The embodiments of the invention in which an exclusive property or privilege is claimed are defined as follows:

TABLE 5

| 1'st sep temp °C. | 2'nd sep temp °C. | 3'rd sep temp °C. | 1'st sep press psig | 2'nd sep press psig | 3'rd sep press psig | 1'st sep wt % feed | 2'nd sep wt % feed | 3'rd sep % feed | wt % feed rec | wt % cat 1'st sep | wt % cat 2/nd sep |
|---|---|---|---|---|---|---|---|---|---|---|---|
| 204 | 197 | >69 | 800 | 37 | 0 | 5.2 | 83.7 | 4.3 | 96.6 | 74.4 | 0.09 |

Before upgrading the purified wax product, the product from the dense gas and/or liquid extractor may be passed in contact with an acidic solid such as alumina or an aluminosilicate zeolite whereupon soluble potassium compounds in the wax are ion-exchanged and basic nitrogen compounds, if present, are absorbed. This subsequently purified wax product can then be directed to further processing such as hydrogenation, hydrocracking, etc. as discussed previously.

The dense gas and/or liquid extraction system described herein can be used either in the batch extraction mode or in the continuous extraction mode. It can be used as the sole means of separating the catalyst/wax mixture or it can be used in combination with one or more other catalyst/wax separation techniques such as 1) settling tanks where the catalyst particles settle to the bottom of a collection tank by gravity, 2) centrifugation devices where the solid catalyst 1. A process for converting synthesis gas including hydrogen and carbon monoxide to hydrocarbons wherein the synthesis gas is contacted with a catalyst in a reaction zone, the catalyst having activity for reducing carbon monoxide is dispersed in a liquid to form a slurry and wherein a hydrocarbon wax is produced in the reaction zone, the improvement comprising:

removing the wax product with a portion of the dispersed catalyst from the reaction zone;

mixing the removed catalyst/wax product with a dense-fluid solvent to extract a portion of the wax into the solvent;

separating the solvent with extracted wax from the dispersed catalyst and residual wax;

reducing the density of the solvent to precipitate a wax product and separating the wax product from the solvent.

2. The process of claim 1 wherein the separated, dispersed catalyst and residual wax are returned to the reaction zone and wherein the solvent, following separation of the wax product, is compressed to increase its density for mixing with fresh catalyst/wax product from reaction zone.

3. The process of claim 2 wherein the separated catalyst is combined into a slurry with hydrocarbon liquid and returned to the reaction zone for conducting a Fischer-Tropsch reaction in the reduction of carbon oxides to hydrocarbons.

4. The process of claim 3 wherein the separated wax product is upgraded in the presence of a zeolite catalyst and a portion of the upgraded wax is added to the catalyst and residual wax prior to return to the reaction zone.

5. The process of claim 2 wherein the dispersed catalyst is selected from the group of Fischer-Tropsch catalysts that are insoluble in the dense-fluid solvent and wherein the solvent is selected from the group consisting of propane, butane, butene, pentane, hexane, toluene and mixtures thereof.

6. The process of claim 5 wherein the dispersed catalyst is selected from the group of Fischer-Tropsch catalysts consisting of the metals or oxides of iron, cobalt, nickel, ruthenium, thorium, rhodium and osmium and further includes a promoter selected from the group consisting of sodium compounds and potassium compounds.

7. The process of claim 1 wherein the catalyst/wax and dense-fluid solvent are introduced tangentially into a settling vessel for separating the dense fluid and its dissolved wax components from the dispersed catalyst and residual wax.

8. The process of claim 1 wherein the mixture of catalyst/wax and dense-fluid solvent are introduced into the lower portion of a separator vessel and the separated solvent is withdrawn from the upper portion of the separator vessel, whereby, any dispersed catalyst and residual wax remaining in the separator vessel are continuously extracted with fresh dense-fluid solvent as catalyst/wax mixture and solvent are continuously introduced.

9. The process of claim 1 wherein the mixture of dissolved wax and dense-fluid solvent is sequentially passed through a plurality of separating vessels in series with reductions in density of the solvent in each successive vessel to fractionate the wax product according to molecular weight.

10. The process of claim 1 wherein the dense-fluid solvent comprises a hydrocarbon formed by the reduction of carbon monoxide in a Fischer-Tropsch reaction.

11. The process of claim 1 wherein the dense-fluid solvent mixed with the catalyst/wax product is at a supercritical pressure and a supercritical temperature.

12. The process of claim 1 wherein the dense-fluid solvent mixed with the catalyst/wax product is at a subcritical pressure and subcritical temperature.

13. The process of claim 1 wherein the pressure of the dense-fluid solvent, after separation from the dispersed catalyst, is reduced to decrease its density and precipitate the wax product from the dense fluid.

14. The process of claim 1 wherein the dense fluid containing dissolved wax is separated from the dispersed catalyst by a density based separation and wherein the wax product is separated from the dense fluid by a second density based separation.

15. The process of claim 14 wherein the dense fluid containing dissolved wax and catalyst particles is exposed to a magnetic field and is passed through a fine particle filter to remove any remaining catalyst particles.

16. A process for converting synthesis gas to hydrocarbons, the synthesis gas containing hydrogen and carbon monoxide in a molar ratio of not more than 1 to 1 obtained from the gasification of coal comprising the steps of gasifying coal to produce $H_2$ and CO, synthesizing $C_1$ to $C_{900}$ hydrocarbons and oxygenates, including wax in the range of $C_{20}$ to $C_{900}$ from $H_2$ and CO in a Fischer-Tropsch slurry reactor containing a slurry of catalyst having carbon monoxide reduction and water gas shift activity, removing the wax along with a portion of the catalyst from the reactor, extracting the wax into an organic solvent to separate the soluble wax from the insoluble catalyst, returning the catalyst to the reactor, decreasing the density of the organic solvent to precipitate the wax and upgrading the wax product to produce hydrocarbon products, gasoline and distillate material.

17. The process of claim 16 wherein the Fischer-Tropsch reactor is maintained at a temperature in the range of about 200° to 320° C. (400° to 600° F.), a pressure in the range of about 3 to 70 atmospheres (50 to 1000 psig), and a space velocity to achieve at least 50% conversion, and all or a portion of the product of the Fischer-Tropsch operation in contact with a ZSM-5 type zeolite conversion catalyst maintained at a temperature in the range of about 200° to 450° C. (400° to 850° F.) and a pressure in the range of about 3 to 50 atmospheres (44 to 735 psig) and recovering as product of the combination operation a high octane gasoline product and a low pour diesel oil.

18. The process of claim 16 wherein the catalyst comprises a Fischer-Tropsch catalyst that is insoluble in the extracting solvent.

19. The process of claim 16 wherein the purified wax product is further treated with an acidic solid to remove potassium and nitrogen compounds from the purified wax.

20. The process of claim 16 wherein the catalyst further comprises a promoter selected from the group consisting of copper and potassium.

* * * * *